United States Patent [19]

Clover, Jr.

[11] Patent Number: 4,693,239

[45] Date of Patent: Sep. 15, 1987

[54] ORTHOSIS

[75] Inventor: William M. Clover, Jr., Trabuco Canyon, Calif.

[73] Assignee: Orthomedics, Inc., Brea, Calif.

[21] Appl. No.: 820,037

[22] Filed: Jan. 21, 1986

[51] Int. Cl.$^4$ .............................................. A61F 5/04
[52] U.S. Cl. ................... 128/80 F; 128/87 R; 128/88; 128/DIG. 15
[58] Field of Search ............... 128/80 R, 80 F, 87 R, 128/88, 89 R, 90, DIG. 15, 83

[56] References Cited

U.S. PATENT DOCUMENTS

| | | | |
|---|---|---|---|
| 3,728,206 | 4/1973 | Buese | 128/90 X |
| 4,041,940 | 8/1977 | Frankel et al. | 128/87 R X |
| 4,057,056 | 11/1977 | Payton | 128/89 R X |
| 4,320,748 | 3/1982 | Racette et al. | 128/80 F |
| 4,454,871 | 6/1984 | Mann et al. | 128/89 R X |
| 4,481,941 | 11/1984 | Rolfes | 128/88 X |
| 4,505,269 | 3/1985 | Davies et al. | 128/87 R |
| 4,553,535 | 11/1985 | Finnieston et al. | 128/88 |
| 4,576,153 | 3/1986 | Zagorski et al. | 128/87 R |

Primary Examiner—Richard T. Stouffer
Attorney, Agent, or Firm—Nilsson, Robbins, Dalgarn, Berliner, Carson & Wurst

[57] ABSTRACT

An orthosis for supporting a limb of a patient having soft tissue damage includes a semi-rigid shell having lateral, medial and posterior portions, and a soft porous pad which surrounds the limb within the semi-rigid shell. The pad and shell are firmly secured around the limb by utilizing hook and pile straps. If the orthosis is utilized for a leg, a footplate is pivotally attached to medial and lateral uprights. The uprights are adjustably secured to the shell, thereby restricting the movement of the foot. An opening is provided in the shell across the anterior part of the limb to reduce the pressure on the damaged soft tissue. The shell supports a fractured limb and the pad provides comfort to the patient and enhances the healing of the damaged soft tissue.

8 Claims, 5 Drawing Figures

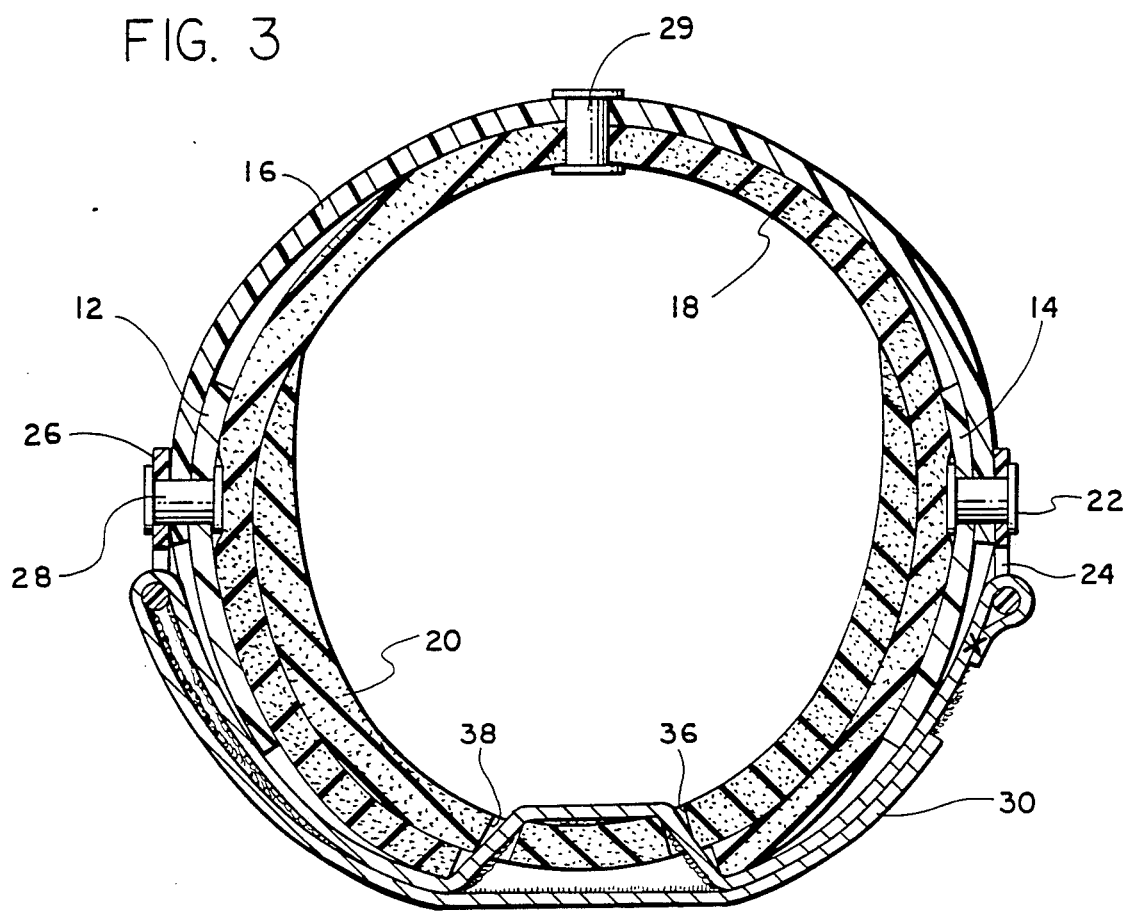
FIG. 3
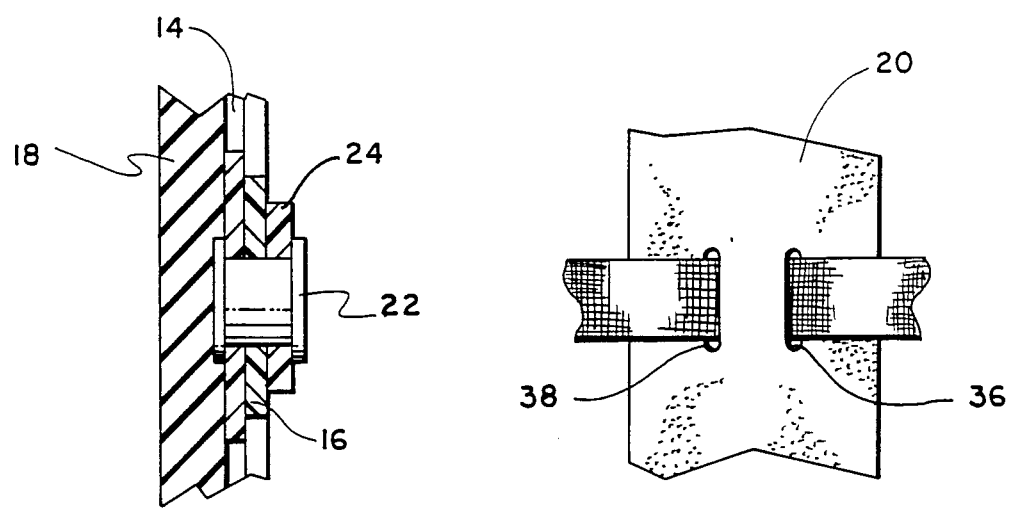
FIG. 4
FIG. 5

ORTHOSIS

BACKGROUND OF THE INVENTION

The present invention relates to fracture bracing and, more particularly, to an improved fracture orthosis or brace of the type that permits ambulation of the patient having both a fracture and soft tissue damage.

Traditionally, fractures of the tibia have been treated with a toe-to-groin cast of plaster of paris. The cast immobilizes the ankle, leg, knee and thigh, thereby severely limiting the mobility of a typical patient. Lack of ambulation can lead to joint stiffening and muscle atrophy. Additionally, the cast is uncomfortable because of its weight, and the patient's inability to relieve itching.

It has been recognized that after an initial period with the toe-to-groin cast a special type of fracture brace or orthosis for tibia and fibula fractures can be used in place of toe-to-groin casts. This fracture brace extends from the foot to the knee and completely encases the involved leg in a rigid shell. An example of this type of fracture brace is described in U.S. Pat. No. 4,320,748 to Racette et al. Loads from the ambulation permitted by this type of fracture brace are transferred to the proximal part of the skeleton by the rigid shell, the encased musculature, and the involved tibia and fibula. It has been found that this load transfer can enhance osteogenesis. Any shortening of the involved leg with this technique is of the same magnitude as with the toe-to-groin cast. Any rotation or angulation of the involved bone is also of the same magnitude.

This prior fracture brace permits proximal joint use, and reduces muscle atrophy and the incidence of non-union of the bones. In the past, the acuteness of the initial injury usually results in appreciable swelling, discomfort, and soft tissue damage for which a toe-to-groin cast would be necessary. The use of the prior fracture brace with soft tissue damage can result in unacceptable discomfort because of pressure on the damaged tissue. Therefore, the fracture brace would be used only after initial acute treatment in a toe-to-groin cast, or after the soft tissue damage has healed.

Toe-to-groin casts require removal to treat soft tissue damage, or to make adjustments necessary for the encapsulation required for the proper fit between the bone, cast, and soft tissue. However, once these casts are removed they cannot be reused. The prior fracture brace can be removed, adjusted, and reused, but it can only be used after soft tissue damage has healed. Therefore, there is a current need for a fracture orthosis or brace which can be used while soft tissue damage is healing.

The present invention is an orthosis which can be used for patients having both a fracture and soft tissue damage. The orthosis of the present invention provides a shell which is rigid enough to support a limb but does not exert excessive pressure to the damaged soft tissue which would cause discomfort. The orthosis of the present invention also provides ventilation to the limb thereby enabling the damaged soft tissue to heal properly and further allows for comfort while wearing the orthosis.

SUMMARY OF THE INVENTION

An orthosis for supporting a limb includes a semi-rigid shell which is open across the anterior part of the limb, and has at least a medial and a lateral portion coupled to each other across the posterior part of the limb. A soft, flexible porous material adapted to surround the limb is disposed within the shell. Means are provided for urging adjacent lateral and medial edges of the shell nearest the anterior part of the limb toward each other, thereby securing the shell and porous material around the limb.

In one embodiment, the orthosis further includes lateral and medial uprights pivotally attached to a footplate. The lateral upright is secured to the lateral portion of the shell while the medial upright is secured to the medial portion of the shell.

Alternatively, the medial and lateral portions of the shell may be coupled to a posterior portion of the shell. The porous material may be a perforated foam pad having a first portion which covers the lateral, medial and posterior parts of the limb, and a second portion which covers the anterior part of the limb.

BRIEF DESCRIPTION OF THE DRAWINGS

The invention will be better understood from the following detailed description thereof taken in conjunction with the accompanying drawings, in which:

FIG. 3 is a cross-sectional plan view of the present invention taken about line 3—3 in FIG. 1, with the foot plate and uprights not being shown;

FIG. 4 is a cross-sectional elevational view of a portion of the shell of the present invention taken about line 4—4 in FIG. 2; and FIG. 5 is an enlarged front view of a portion of the tongue pad showing a strap threaded through the slots.

DETAILED DESCRIPTION OF THE PREFERRED EMBODIMENT

Figure 1:
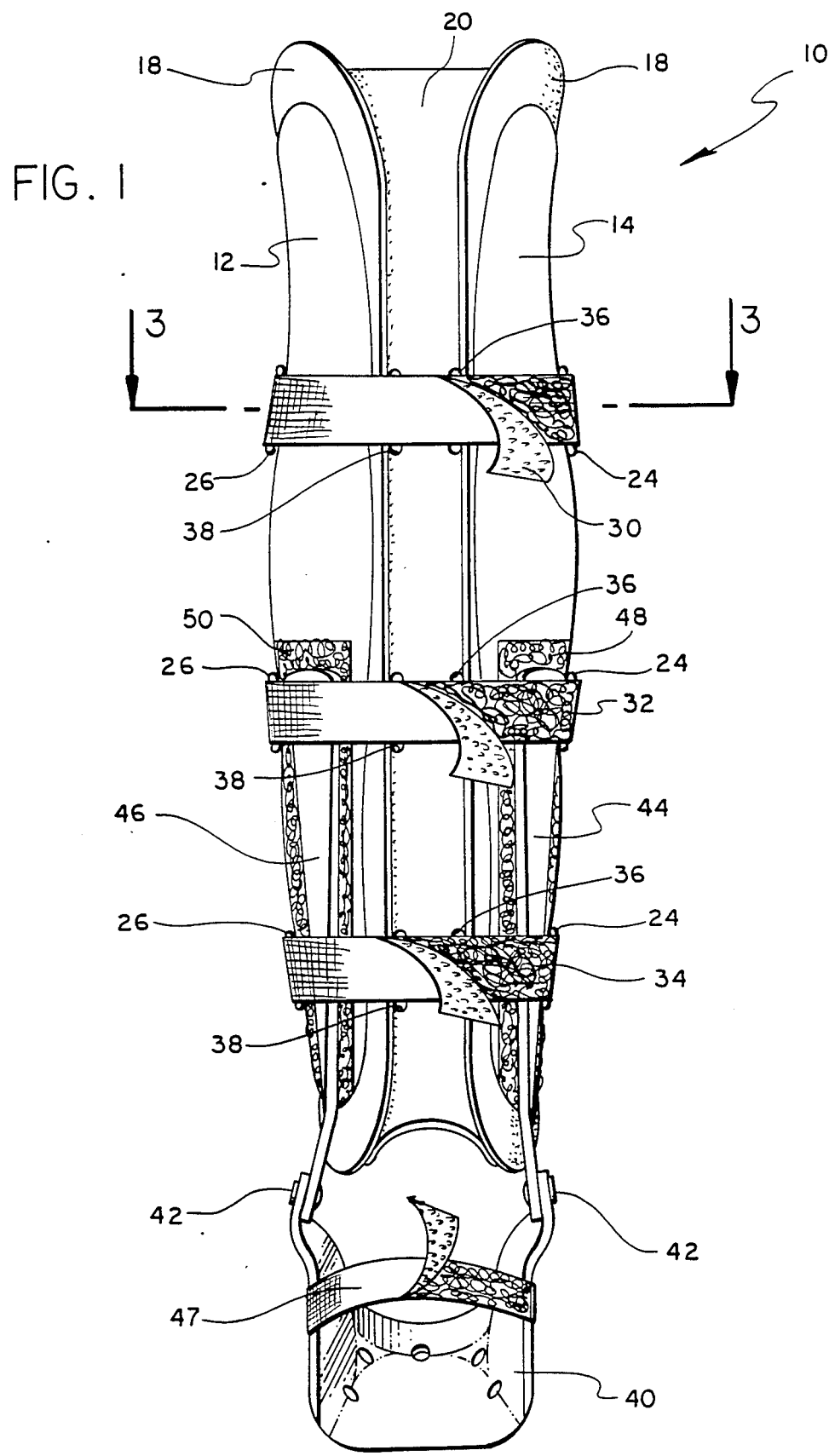
FIG. 1 is a front elevational view of the present invention.
Figure 2:
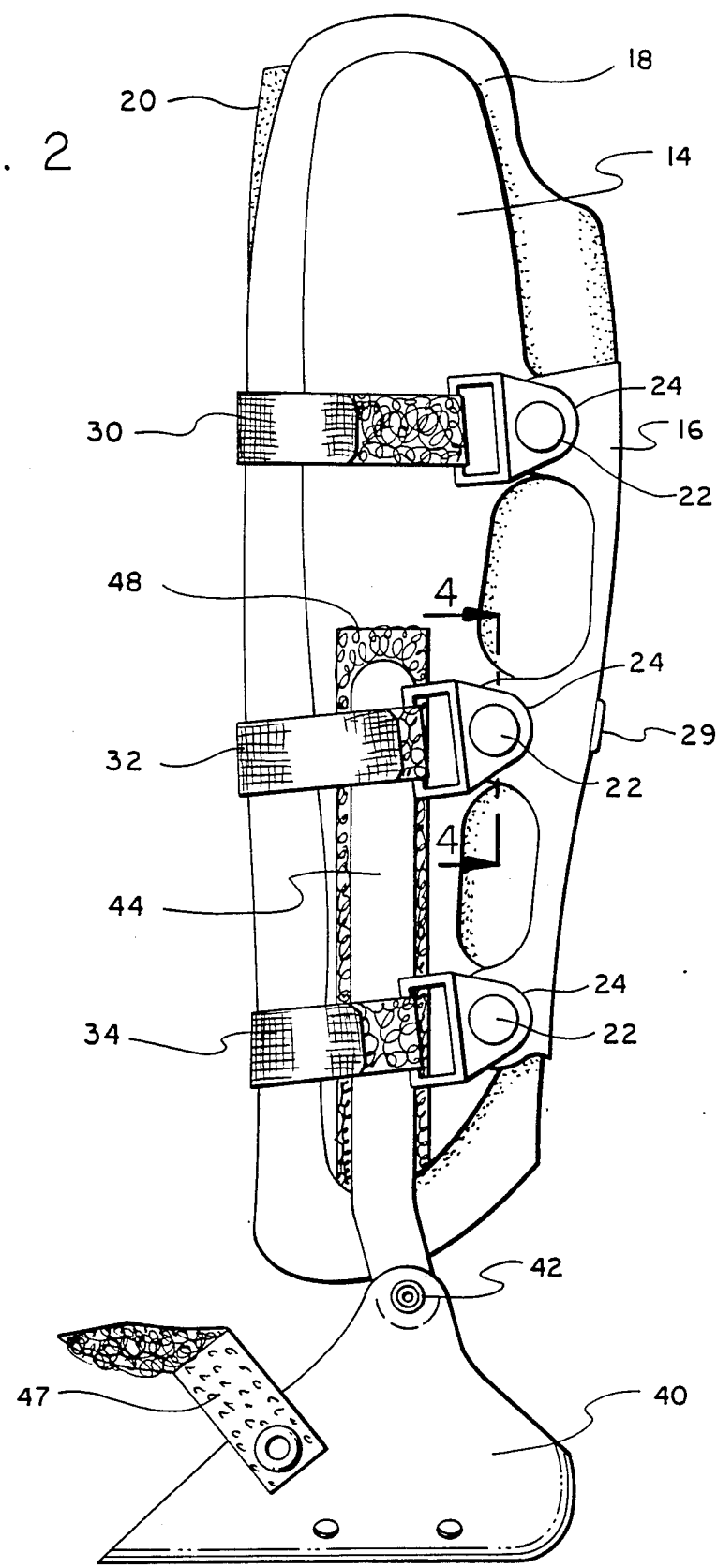
FIG. 2 is a side elevational view of the present invention shown in FIG. 1.

FIG. 1 shows an orthosis 10 of one embodiment of this invention for supporting the lower part of a leg. A lateral shell portion 12 and a medial shell portion 14, generally having the shape of the leg between the knee and the ankle, are connected by a posterior shell portion 16 which is shown in FIGS. 2 and 3. The posterior shell portion 16 generally has the shape of the posterior part of a leg from above the ankle to the top of the calf. The lateral, medial and posterior shell portions are formed of a hard, resilient material, such as polyethylene. These shell portions form a shell having an opening across the anterior part of the leg. This opening provides the flexibility needed to reduce excessive pressure to the damaged soft tissue.

A pad 18, which is made of soft porous material, covers the lateral and medial parts of the leg generally from the ankle to the knee and covers the posterior part of the leg generally from above the ankle to below the knee. Therefore, the pad 18 also has an opening across the anterior part of the leg generally matching the opening defined by the shell. A front tongue pad 20, which is made of the same material as the pad 18, covers the anterior part of the leg and partially covers the lateral and medial parts of the leg. The pad 18 is placed inside the lateral, medial and posterior shell portions 12, 14 and 16, respectively. The front tongue pad 20 is placed over the opening between the edges of the pad 18 with the edges partially covering the lateral and medial parts of the leg being placed inside the pad 18 as can be seen in FIG. 3. Therefore, by utilizing both the pad 18 and front tongue pad 20, the leg is completely surrounded by a soft, porous pad material.

Referring to FIGS. 2, 3 and 4, the medial shell portion 14 is attached to the posterior shell portion 16 by fasteners such as plastic rivets 22. The plastic rivets 22 also attach a plurality of D-rings 24 to the posterior shell portion 16. Lateral shell portion 12 is similarly attached to the posterior shell portion 16, and a second plurality of D-rings 26 are attached to the posterior shell portion 16 by plastic rivets 28. Additionally, pad 18 is attached to the posterior shell portion 16 by plastic rivet 29, shown in FIGS. 2 and 3.

Straps 30, 32 and 34 tighten the shell portions and pads around the leg. These straps can be of the belt and buckle type, or hook and pile fasteners such as those sold under the trademark "Velcro", as shown in the preferred embodiment. The pile end of each strap is attached to a D-ring on either the lateral shell portion 12 or medial shell portion 14. Each of the hook ends of the straps are then drawn towards the front tongue pad 20 and threaded through slots 36 and 38 disposed in the front tongue pad 20, as shown in FIG. 5. The hook ends of each strap are then drawn towards the D-rings on the other side, is threaded through these D-rings and doubled back onto themselves to be fastened on the pile ends.

If the patient wearing the orthosis has a fracture, the foot must only be limited to a back and forth motion. Any rotational movement of the foot about the ankle must be prevented. Therefore, as is shown in FIGS. 1 and 2, the orthosis 10 is provided with a footplate 40 pivotally attached by rivets 42 to a medial upright 44 and lateral upright 46. The hook end of a hook and pile strap 47 is attached to one end of the footplate 40 while the pile end is attached to the other end of the footplate. The hook and pile ends are fastened together to prevent distal migration of the orthosis.

To accommodate the requirements of a particular patient the foot plate must be allowed an infinite number of positions within predetermined ranges. Therefore, the medial upright 44 and lateral upright 46 are attached to the medial shell portion 14 and lateral shell portion 12, respectively, by hook and pile fasteners. Individual pile fastener sections 48 and 50 are firmly secured to medial shell portion 14 and lateral shell portion 12, respectively. Individual hook fastener sections (not shown) are firmly secured to the inside of the medial upright 44 and lateral upright 46. The foot plate and uprights are of the same type described in U.S. Pat. No. 4,320,748 to Racette et al.

The leg orthosis described is typically fitted on a patient by the following procedure. The front tongue pad 20 is removed away from the pad 18 to expose the opening defined by the shell portions 12, 14 and 16 and pad 18. The medial and lateral uprights 44 and 46 are removed from the medial and lateral shell portions 14 and 12, respectively. The orthosis is fitted around the patient's leg covering the lateral, medial and posterior parts of the leg, thereby leaving the anterior part of the leg exposed. If necessary, the orthosis is marked for any trim lines. The orthosis is removed from the patient's leg and trimmed along the marked trim lines. Alternatively, pad 18 or front tongue pad 20 may be heat molded for individual fit, and shell portions 12, 14 or 16 may also be heat molded. The orthosis is again placed on the patient's leg as previously described and using mild pressure, the footplate 40 is inserted against the heel of the foot until it is seated firmly. Strap 47 is then firmly attached across the dorsum of the foot by fastening the hook and pile ends together. Medial upright 44 and lateral upright 46 are pressed firmly on pile sections 48 and 50, respectively. The front tongue pad 20 is placed over the anterior part of the leg and the portions which partially cover the lateral and medial parts of the leg are placed inside the pad 18. Straps 30, 32 and 34 are then firmly tightened by threading each of the hook ends through slots 36 and 38 in the tongue pad 20, D-rings 26, doubling back on themselves and fastening them to the respective pile ends.

Since the orthosis of the present invention does not have an anterior rigid shell, and provides a soft pad which surrounds the limb, a greater amount of flexibility is achieved. This flexibility greatly reduces pressure on any soft tissue damage. Additionally, the pads 18 and 20 reduce any discomfort to the patient. The pads are preferably perforated foam, thereby allowing more ventilation to the limb to enhance the healing of the soft tissue damage. The minimal amount of rigid shell material utilized in the present invention also enables a patient having compound fractures to wear the orthosis.

Although the orthosis has been described as being used for the lower portion of the leg, it can be modified to be used for any part of the limb. For example, by eliminating the foot plate and uprights assembly, the shell portions and pads can be shaped to be used on the upper or lower part of an arm. Similarly, an orthosis shaped for the upper part of a leg can be used in conjunction with the orthosis described for the lower part of the leg. The two leg components can then be attached to each other.

Another use of the orthosis of the present invention is as an intermediate step for a patient who has just had a cast removed. Many individuals are not confident to move or use an injured limb soon after a cast is removed. These individuals would like a little protection or support to help them gain confidence in using the previously injured limb. Therefore, an orthosis which is flexible yet provides some protection and support would be required. The orthosis of the present invention does provide this flexibility and support and thus could be used for this purpose.

From the foregoing, it has been shown that the present invention provides an orthosis which allows its use for a patient having soft tissue damage, and further allows its use after an individual no longer requires a cast. Although a specific embodiment has been illustrated and described, various modifications and changes may be made without departing from the spirit and scope of the invention. For example, the lateral shell portion 12, medial shell portion 14 and posterior shell portion 16 may be manufactured as a unitary shell instead of three separate components.

What is claimed is:

1. A lower leg orthosis for supporting the lower leg comprising:
   a semi-rigid shell provided with an anterior opening, such that said shell is open across that area of the shell where the anterior part of the leg is adapted to be positioned, and having posterior, medial and lateral portions, the medial and lateral portions each being coupled to the posterior portion;
   a first soft flexible material, more flexible than the semi-rigid shell, being disposed within said shell and adapted to enclose the lateral, medial and posterior parts of the leg;

a second soft flexible material, said second material having substantially the same flexibility as the first flexible material, said second material also being more flexible than said semi-rigid shell, said second material being wider than the width of said anterior opening when the orthosis is positioned on a leg so as to be adapted to be disposed partially within said shell and to enclose the anterior part of the leg, the exposed portion of said second flexible material being free of any additional material which substantially decreases its flexibility; and means for urging the lateral and medial shell parts toward each other to secure said shell and flexible materials around the leg.

2. The orthosis as defined in claim 1 wherein said first and second materials are soft and porous.

3. The orthosis as defined in claim 2 wherein said first flexible material comprises a heat moldable perforated foam pad and said second flexible material comprises a heat moldable perforated foam pad.

4. The orthosis as defined in claim 3 further comprising:

a footplate;

lateral and medial uprights pivotally attached to said footplate; and means for securing said lateral upright to said lateral portion of said shell, and said medial upright to said medial portion of said shell.

5. The orthosis as defined in claim 4 wherein said urging means includes a plurality of straps attached vertically along said shell and extending across said second flexible material.

6. The orthosis as defined in claim 5 wherein said securing means includes hook and pile fasteners.

7. The orthosis as defined in claim 1 wherein:

said lateral and medial portions are coupled to said posterior portion by a plurality of rivets; and said urging means includes a plurality of straps fastened along one side of said shell, said straps extending across the anterior of the limb to attach to the other side of said shell.

8. The orthosis as defined in claim 1 wherein edge portions of said second flexible material are adapted to be placed inside said first flexible material.

* * * * *

UNITED STATES PATENT AND TRADEMARK OFFICE
CERTIFICATE OF CORRECTION

PATENT NO. : 4,693,239

DATED : September 15, 1987

INVENTOR(S) : William M. Clover, Jr.

It is certified that error appears in the above-identified patent and that said Letters Patent are hereby corrected as shown below:

IN THE SPECIFICATION:

Column 4, line 26, before "limb", delete "the" and insert --any--.

Signed and Sealed this

Twenty-third Day of February, 1988

Attest:

DONALD J. QUIGG

*Attesting Officer*     *Commissioner of Patents and Trademarks*